(12) United States Patent
Summit

(10) Patent No.: US 7,797,072 B2
(45) Date of Patent: Sep. 14, 2010

(54) PROSTHETIC LIMB WITH REPLACEABLE FAIRING

(75) Inventor: Scott Summit, San Francisco, CA (US)

(73) Assignee: Bespoke Innovations, Inc., San Francisco, CA (US)

( * ) Notice: Subject to any disclaimer, the term of this patent is extended or adjusted under 35 U.S.C. 154(b) by 346 days.

(21) Appl. No.: 11/973,069

(22) Filed: Oct. 5, 2007

(65) Prior Publication Data

US 2009/0093891 A1    Apr. 9, 2009

(51) Int. Cl.
*G06F 19/00* (2006.01)
*A61F 2/54* (2006.01)

(52) U.S. Cl. .................. 700/119; 700/98; 700/182; 700/212; 623/29; 623/57; 623/66.1

(58) Field of Classification Search ............... 700/159, 700/95, 98, 117–119, 182, 197, 207, 212; 703/1, 6, 7, 11; 382/131, 154; 623/27, 29, 623/57, 65, 66.1

See application file for complete search history.

(56) References Cited

U.S. PATENT DOCUMENTS

| | | | | |
|---|---|---|---|---|
| 5,741,215 A | * | 4/1998 | D'Urso | 600/407 |
| 5,880,964 A | * | 3/1999 | Schall et al. | 700/159 |
| 5,888,216 A | * | 3/1999 | Haberman | 623/36 |
| 2002/0016631 A1 | * | 2/2002 | Marchitto et al. | 623/7 |
| 2004/0236424 A1 | * | 11/2004 | Berez et al. | 623/14.12 |
| 2005/0043835 A1 | * | 2/2005 | Christensen | 700/98 |

\* cited by examiner

*Primary Examiner*—Sean P Shechtman
(74) *Attorney, Agent, or Firm*—Dergosits & Noah LLP

(57) ABSTRACT

A prosthetic limb has an outer surface that is a mirror image of an intact limb. The intact limb is scanned and the surface data is manipulated to create a virtual mirror image. The end of the amputated limb is also scanned to obtain socket data. A virtual limb is designed using a computer program based upon the mirror image and end of the amputated limb data. The computer program is also used to design a removable fairing that provides color and texture to the prosthetic limb.

24 Claims, 12 Drawing Sheets

PROSTHETIC LIMB WITH REPLACEABLE FAIRING

BACKGROUND

A prosthesis limb replaces a missing extremity, such as an arm or a leg and may be needed for a variety of reasons, including diseases, and accidents. An artificial limb may also be needed when a person is born with a missing or damaged limb(s). The type of prosthesis limb used is determined largely by the extent of an amputation or loss and location of the missing limb. A transtibial prosthesis is an artificial leg that is attached to a user below the knee and includes a lower leg, ankle and foot. The transfemoral prosthesis is an artificial leg that is attached to the user's amputated limb above the knee and includes an upper leg and mechanical knee. A transradial prosthesis is an artificial arm that is attached to the user below the elbow and includes a forearm and hand. A transhumeral prosthesis is an artificial arm that is attached to the user above the elbow.

In developing areas of the world, including large portions of Africa, the leading causes of amputations are industrial, vehicular, and war related accidents. In more developed areas, such as North America and Europe, the leading causes for the amputations are diseases including cancer, infection and circulatory. In the United States, approximately 100,000 legs are lost each year to diabetes, vascular disorder, accidents and cancer. Because there are so many amputations, there is a substantial need for prosthetic limbs.

The engineering of prosthetic limbs has improved greatly. In particular, artificial knees and feet have been developed for prosthetic legs that provide increased mobility and functionality. While the engineering and mechanics of prosthetic limbs have evolved greatly, very little thought has been given to the aesthetics of the human being for whom the device was intended. With reference to FIG. 1, a modern prosthetic leg 101 is shown having a socket 121 that has a recessed surface that engages the end of the user's amputated leg. The socket 121 is typically a padded plastic structure that distributes the compression forces on the end of the amputated limb. The bottom of the socket 121 is attached to a pylon 123 which is a tubular support that can be made of titanium or aluminum. The pylon can be manufactured through an extrusion process. The bottom of the pylon 123 is attached to an artificial foot 125 that can be a molded plastic structure. The prosthetic leg 101 may also have a foam covering 127 and can be attached to the socket 121 and pylon 123 to provide a more uniform shape. The various socket 121, pylon 123 and foot 125 can be coupled together using fasteners including bolts, screws and adhesives.

A problem with the existing prosthetics is that they neglect the fundamental symmetry of the human form. Symmetry is a visible indication of the health of the individual and asymmetry can be perceived as a health shortcoming. Many medical conditions such as a nervous tick, stroke, leprosy, elephantitis, etc. are exhibited in patients as an asymmetric appearance. Similarly, the asymmetric nature of existing prosthetic limbs communicates that a user has a 'medical necessity' and reinforces a message that the wearer is damaged or defective.

For many amputees the asymmetric appearance of the prosthetic limb is more troublesome than their physical discomfort. The task of disguising the asymmetric appearance of the prosthetic limb is nearly impossible because the socket 121, pylon 123 and foot 125 used to create the prosthetic limb are a collection of parts from a variety of manufacturers. The socket is a custom fabricated part, usually hand made from carbon fiber and a binder. The patient outgrows the socket every few months or years and the socket needs to be replaced periodically. Because the components are not specifically designed for left or right sides of the body or have the appearance of a human leg, the components cannot have a symmetric appearance.

Efforts to improve the appearance with a flesh colored electrometric foam cover 127 are also problematic. While the diameter of the cross section may be more uniform than the socket 121, pylon 123 and foot 125, the cover 127 is not an accurate dimensional representation of a human leg. The simulated human flesh is typically not life like and can connote dead tissue.

What is needed is an improved prosthetic limb that is symmetrical in form and also allows the user to change and personalize the appearance.

SUMMARY OF THE INVENTION

The present invention is directed towards an improved prosthetic limb that has the physical dimensions that match the user's intact limb and can also include a removable fairing that allows the user to personalize and change the appearance of the limb. The prosthetic limb and fairing are created by a prosthetic designer using computer aided design (CAD) software and computer controlled fabrication processes. While the prosthetic limb is described as a leg, the same processes can be used to fabricate prosthetic arms, and as such, prosthetic arms are intended to fall within the scope of the present invention.

The designer first creates a template for a virtual limb and fairing using a computer aided design system. The design of the prosthetic leg can include a upper leg, knee, lower leg, and foot. If the user has a sound side leg, a prosthetic leg having a matching outer surface can be designed. In order to accurately create a matching prosthetic leg, the surface of the user's intact leg is first measured. The measurement of the intact leg is preferable done with an optical measuring device. For example, a laser measuring device can be used to scan the intact leg and obtain measurements for surface points across the entire leg that is a digital representation of the outer surface. Examples of laser scanners that are suitable for scanning the leg include units available from Polhemus, HandiScan 3D and Thinglab. Alternatively, the leg can be measured through other means. The digital scan data can then be converted into surface that can be used by the CAD system. An example of this scan data conversion software is available from GeoMagic. A digital representation of the intact leg surface can then be manipulated by the CAD software to create a mirror image of the intact limb that will be used as the outer surface data for the prosthetic limb. The prosthetist can use a custom CAD application to join the mirror image surface to the other components of the prosthetic leg and display the assembled prosthetic leg. A suitable CAD software for prosthetic and fairing design is available from but not limited to Pro/Engineer and SolidWorks. As discussed in the background, for aesthetic and emotional reasons, it is important that the prosthetic limb have a symmetric appearance to the intact leg.

The socket shape must correspond very closely to the end of the amputated limb in order for the prosthetic leg to be comfortable when worn. The socket design data is typically provided by a prosthetist. Like the leg surface data, the socket design data can be obtained through optical scanning of the end of the amputated limb. Alternatively, the end of the amputated limb can be measured manually with various mechanical measuring devices. These measurements are used to create a socket surface shape that is substantially the reversed shape of the end of the amputated limb. The socket design may also factor in padding materials that are placed between the amputated limb and the socket wall. The socket will be covered with a 'thigh' fairing panel.

In addition to the mirror image intact limb data and the socket data, the prosthetic leg requires a foot component and a fairing. In an embodiment, feet are stock items that are manufactured in various sizes and models. Some feet have energy storing members that allow the user to run more efficiently. Alternatively, the feet can be sized to match the intact foot. Digital representations of the stock feet components can be stored in a database that is accessible to the design system. The custom geometry for the fairing surfaces for the foot can be obtained, like the other fairing surfaces, by creating mirror image data of the user's intact foot through a laser scanning process as described above.

The prosthetist uses the CAD based application to combine the leg surface data with socket and foot data to create a complete virtual prosthetic leg that is displayed on the computer. The GUI can allow the prosthetic leg components to be easily changed using integrated design tools. These GUI controls can allow the prosthetic designer to alter the prosthetic design in various ways to customize various attributes of the design within parameters designated by variables built into a leg template. A GUI tool can be used, for example, to change the foot component used with the leg. The GUI tool can also be used to modify the leg to include specific colors, textures and surface features. Thus, the user can create a prosthetic leg that is substantially a mirror image to the intact leg or create a leg that is very different in appearance.

In an embodiment, the prosthetic leg can also include a fairing that is a removable layer that covers a portion of the prosthetic leg. The user can specify the aesthetic attributes of the fairings which can also be removed or replaced The user can also alter the appearance of a portion of the prosthetic leg. The appearance of the fairing and leg can be easily changed as desired by the user. The CAD system can also allow the user, the prosthetic designer and the prosthetist to view the prosthetic leg with various fairing designs. For example, the GUI can include a fairing material controller that allows the user to see many virtual fairings made from a variety of materials including: metals, plastics, fabrics, leather, etc. The prosthetic designer can also use the CAD system to select the attachment mechanism for the fairing. The attachment mechanism can include adhesives, fasteners, magnets, etc The fairing must be securely attached to the prosthetic leg to remain attached during normal physical activities. The CAD system is particularly useful because it allows the user to design and view any desired combination of features and fairings prior to fabrication.

In addition to the physical appearance, the prosthetic leg must also be strong enough for the required use. A prosthetic leg must be able to support the user's weight and impact while running or jumping and a prosthetic arm must be able to withstand the normal use forces. In an embodiment, the strength of the prosthetic limb can be provided by internal structures such as a load bearing pylon. An outer surface that is not load bearing can be attached around the load bearing pylon. Alternatively, the load bearing structure can be a much larger volume component that not only has a load bearing core that connects the knee component to the foot component and expands outward so that it creates a sense of the volume defined by the original leg. In order to create a lighter structure, void space can exist within the outer surface. The space between the pylon and outer surface can be a lattice, a series of ribs, a channel, or any sculptural element that may function to reduce weight, enhance appearance, and create the sense of leg volume and shape. In other embodiments, the limb is fabricated with the outer surface functioning as a load bearing member. Because the materials used to fabricate the prosthetic limbs are very strong, the system can be used to design a template, an external surface that is a thin wall and an internal structure that adequately supports the expected loads and the outer surface wall.

The CAD system can be used to design the load bearing member of the prosthetic leg. The prosthetic designer can input the weight and activity level of the user into the CAD system and the required strength can then calculate based upon expected loads. The CAD system can then design a load bearing structure that will be able to support the load requirements. As discussed above, the load bearing member can be an internal elongated structure that supports the entire load or alternatively, an integrated design in which the entire structure is load bearing. The CAD system can be used to design a load bearing structure that has the required strength for both the internal load bearing or integrated configurations.

The CAD system can also provide information to the prosthetic designer that may be important to the prosthetic leg design. For example, the weight of the prosthetic leg will vary depending upon the required strength, the volume of material needed and the density of the material. Once the design is completed, the volume of material and weight can be determined. The weight of a fairing can similarly be determined based upon the volume of the design and materials selected by the user. The system can display the estimated weights for the leg and fairings during the design process. The prosthetic designer can determine if the weight is suitable for the user. If not, the design of the prosthetic leg and fairing may be modified to use lighter weight materials. Ideally, the leg should be as light as possible while providing the required strength for the user.

Once the design is finalized, the design data produced by the CAD system can be used to fabricate the prosthetic leg and fairing. In an embodiment, the prosthetic leg can be fabricated as one or more non load bearing components that surround an internal load bearing member that supports the user's weight. Alternatively, the leg can be fabricated as an integrated structure having an outer surface that is part of the load bearing member. The integrated construction prosthetic leg can be a completely hollow monocoque design or have an exterior shell coupled to an internal framework that can provide additional mechanical strength. The design data can include a series of cross sections that define outer wall and any internal framework along the length of the prosthetic leg which is used to fabricate the prosthetic leg.

In the preferred embodiment, the prosthetic leg is fabricated through a rapid prototyping process that uses an energy beam directed at a bath of material. Similar fabrication processes are known as additive manufacturing, rapid manufacturing, layered manufacturing, 3D printing, laser sintering, and electron beam melting (EBM) These fabrication processes use an energy beam that is deflected across the material and causes the exposed material to harden. Another possible manufacturing process is fused material deposition (FDM).

The cross section design data is used by the fabrication machine to construct each of the leg components in a sequential series of layers. As each layer of material is hardened, the completed portion of the leg component is moved vertically into the bath and the next cross section layer is formed and fused to the adjacent formed layer. When all layers are formed, the leg component is completed. In an embodiment, the lower leg, upper leg, socket and fairings can be fabricated as separate components that are assembled to create the prosthetic leg. Since the foot and knee may be off the shelf components, these parts may not need to be fabricated.

The fairing fabrication method will depend upon the selected materials and design. If the fairing is made of a thin flexible material such as leather, the fairing design data can be used by a computer controlled cutting machine to precisely cut the fairing material to the design shape. Alternatively, the fairing can be fabricated from a flexible plastic material or sheet metal to form a three dimensional fairing that can match the contours of the outer surface of the prosthetic leg using the rapid prototyping methods described above. It is also possible to combine different fairing components and customizing the appearance of the cosmetic fairing components. For example, a curved plastic fairing can be covered with a thin flexible material such as leather.

Additional processing of the leg components and fairing can be performed prior to assembly to obtain the desired appearance. Surface treatments can include metal plating, painting, covering, texturing, etc. For example, if a metal finish is specified, the components can be plated with a layer of metal using known metal layer deposition processes. Additional surface processing can be applied to the metal layer. For example, the metal layer can be brushed, polished, sand blasted, etc.

The prosthetic leg can be assembled once all of the components are formed and the surface finishes are applied. The fairing can be attached to the leg with an adhesive or mechanical fasteners. For example, a leather piece can be attached to the plastic fairing panel with adhesive and the fairing panel can be attached to the prosthetic leg with mechanical mounting components, or an 'over center' snap geometry. Alternatively, the fairing may be clamped around the prosthetic leg if it is more rigid and surrounds a portion of the leg. The prosthetic leg may also include surface features that function to hold the fairing in place. For example, a recess that corresponds to the edge of the fairing can be formed in the outer surface.

BRIEF DESCRIPTION OF THE DRAWINGS

The invention will be more fully understood by reference to the following detailed description of the invention in conjunction with the drawings.

DETAILED DESCRIPTION

The present invention is a prosthetic limb having an exterior surface that matches the surface contours of a human limb. The prosthetic limb emulates the contours of the original limb by referencing surface geometry drawn from the sound side limb. The exterior surface can also be modified so a user can alter the appearance of the prosthetic limb. A replaceable fairing can be designed to cover a portion of the prosthetic limb. The prosthetic limb and fairing are designed on a computer and the design data can be used to fabricate the prosthetic components using computer controlled fabrication machines. The inventive prosthetic limb is primarily directed towards prosthetic legs but the same design and fabrication processes can also be used to create prosthetic arms. The prosthetic limb is preferably designed by an industrial designer using a Computer Aided design (CAD) program.

The inventive prosthetic legs include a load bearing component that functions as the human tibia. The upper end of the load bearing component is attached to a socket that engages the end of the amputated limb and the lower end of the load bearing component is coupled to an artificial foot. The part of the fairing that covers the foot region can be flexible and allow for movement between the load bearing component and the artificial foot. The mechanical data for the prosthetic leg that may include the relative positions of the socket, knee and foot as well as the movement of these components can be provided by a prosthetist. This mechanical data is input into a CAD program that is referenced to design the rest of the prosthetic leg. An example of a suitable CAD program is Pro/Engineer by Parametric Technology Corporation. Other CAD software includes: SolidWorks by SolidWorks Corporation a subsidiary of Dassault Systèmes, S. A.

Figure 1:
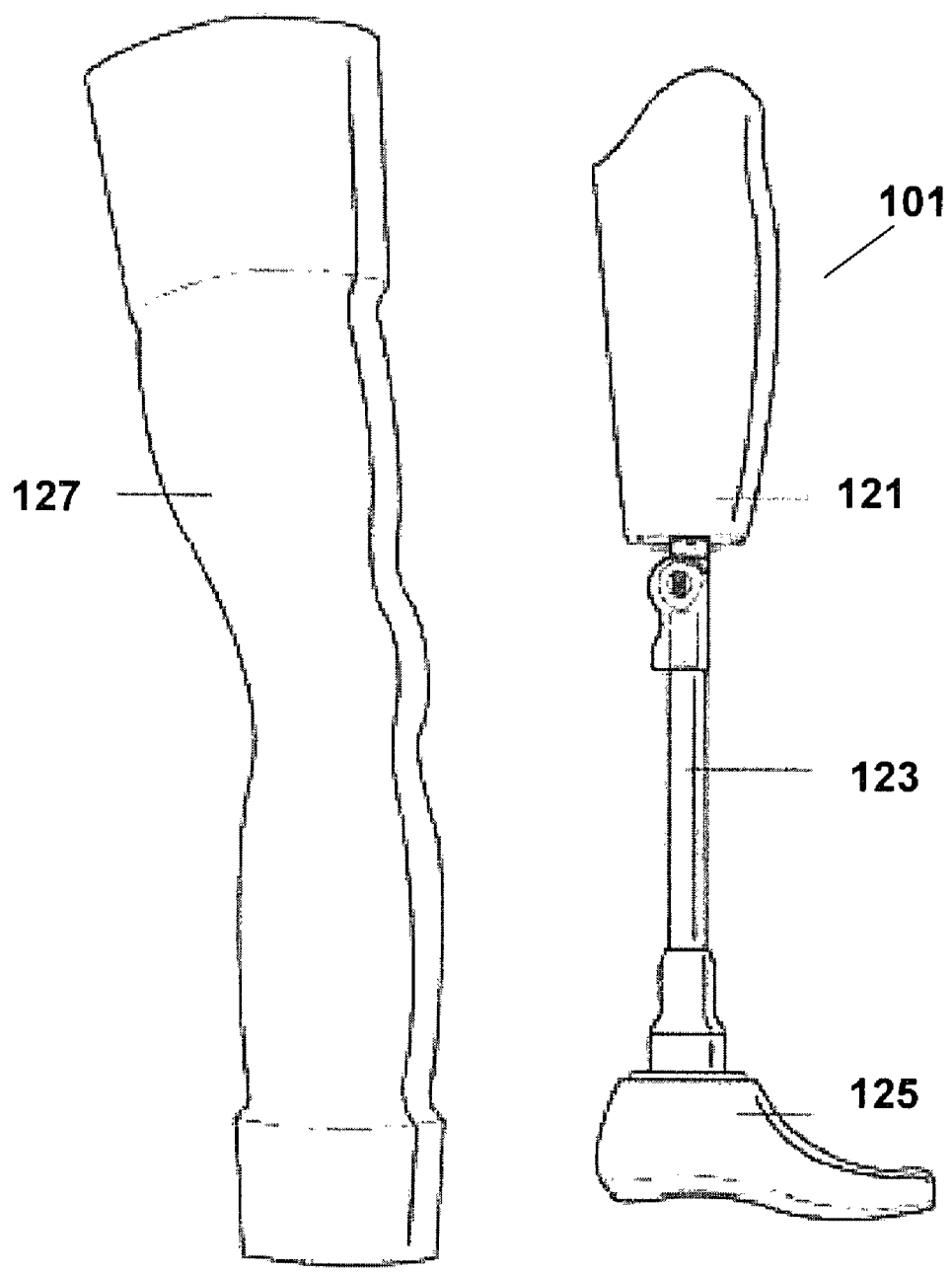
FIG. 1 is a view of a prior art prosthetic leg.
Figure 2:
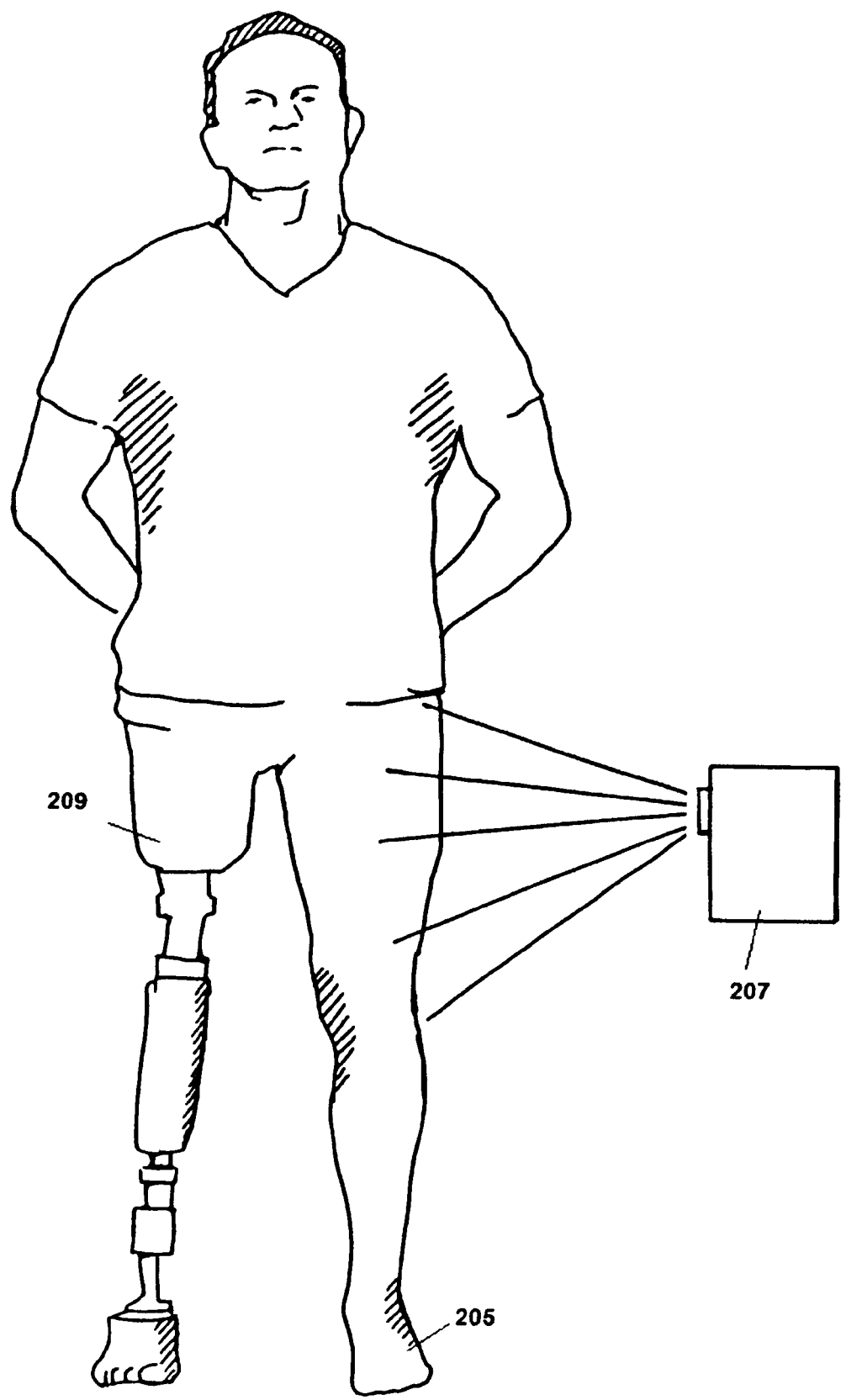
FIG. 2 is a view of a scanning device used to measure an intact leg.

In a preferred embodiment, at least some part of an exterior surface of the prosthetic leg is a mirror image that is matched to the user's intact leg. The surface data of the intact leg can be obtained through a laser scanning process and input into the CAD program. With reference to FIG. 2, the intact leg 205 is scanned with a three-dimensional laser scanner 207. The leg 205 must be scanned from multiple sides to obtain a full three dimensional digital image. The scanner 207 creates a data set of geometric measurements for many points on the surface of the leg 205. The accuracy and detail of the three dimensional digital image is improved by taking more measurements of the leg 205. In addition to obtaining data for the intact leg 205, the described laser scanning method can also be used to obtain the surface measurement data for the end of the amputated limb 209. The scanner 207 may also include photo detectors that are used to collect color information so that the exact color(s) of the intact leg 205 can be determined and used to create the prosthetic leg. Suitable handheld laser scanners include the FastSCAN system by Polhemus and the Handyscan 3D system by Handyscan. While optical scanning is the preferred method for determining the surface of the intact leg, in other embodiments any other optical, electomagnetic or mechanical method can be used to obtain this information. While some scanning systems are capable of detecting a surface contour with a resolution less than a millimeter, the described scan does not require this level of accuracy to recreate the appearance of the intact leg.

The scan data is converted into a usable surface file that can be read by the CAD program. More specifically, the surface data from scan of the intact leg 205 may be referenced in order to extrapolate the shape of the intact leg 205 through a reconstruction process. The reconstruction process uses an algorithm that connects the adjacent points, known as a point cloud, with lines from the scanned leg data to construct a continuous surface from many small polygon shapes that form a polygon model. The data produced by the reconstruction process is a continuous three dimensional digital representation that closely matches the surface of the intact leg 205. The same reconstruction process can be used to obtain the surface data for the end of the amputated limb 209. An example of the software used to perform the scanner data reconstruction process is Geomagic Studio by GeoMagic and Pro Scan Tools which is a plug in module for Pro/Engineer by Parametric Technology Corporation.

The reconstruction surface file for the intact leg is input into the CAD program. The prosthetic designer can use the CAD program to reverse mirror and manipulate the intact leg data to create a mirror image digital representation. This mirror image data can then be used in the design the exterior surface of the prosthetic leg. The leg and socket data are used to form the outer surfaces of the prosthetic leg. The sound side leg geometry is referenced in the creation of the exterior prosthetic surfaces, while the socket data is referenced while the inside of the 'thigh' fairing component is created.

Figure 3:
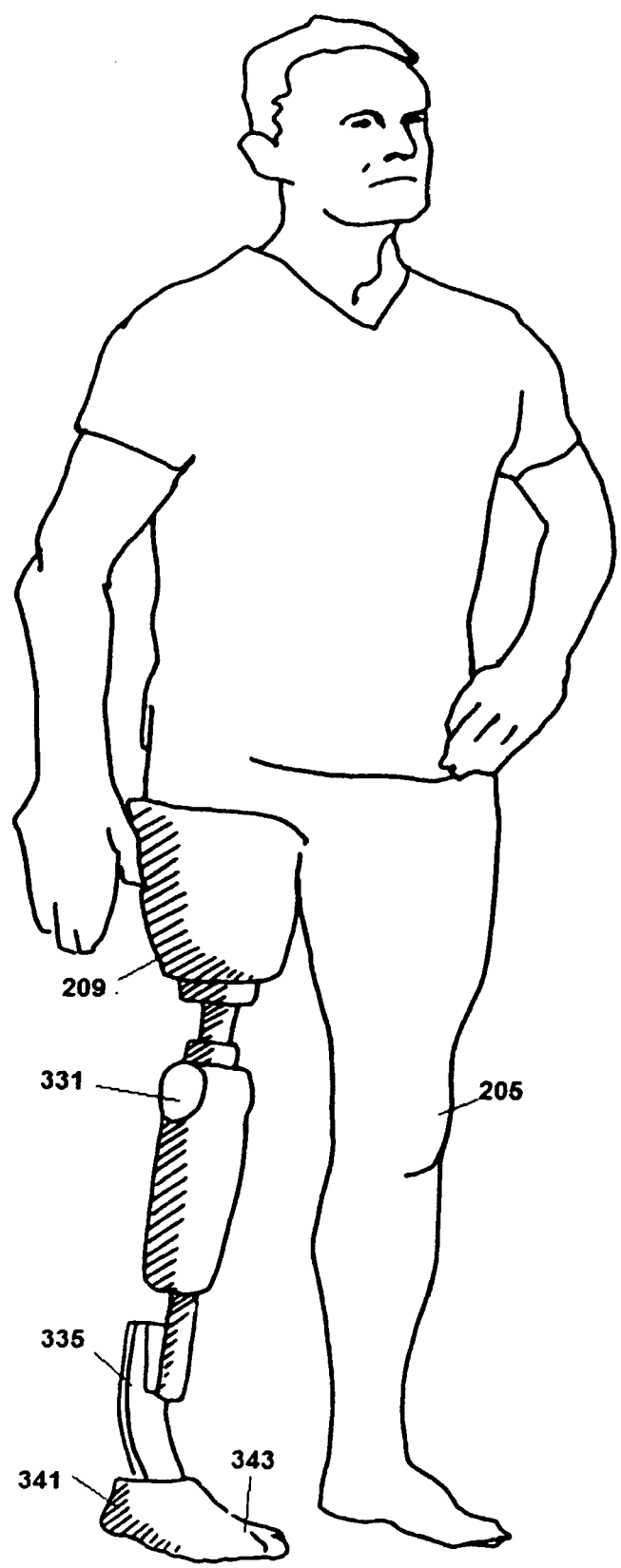
FIG. 3 is a view of load bearing components of a prosthetic leg.

Mechanical components are also required for a fully functional design. With reference to FIG. 3, the user can consult with a prosthetist to determine the exact relative placement of the artificial knee 331 and foot 335 in relation to the end of the amputated limb 209. The prosthetist can use the measurement of the intact leg 205 and use this information as a starting point to determining the relative positions of the socket, artificial knee 331 and foot 335 in the prosthetic leg.

The knee 331 can be a stock item that may include a single pivot with robotic assist, or a multiple linkage assembly that mimics the movement of a human knee. Different knees may be required for different sized patients and different types of expected use. The dimensions and movements of these knees can be stored in a computer data store. The prosthetist may select the most appropriate knee for the patent and a digital representation of the selected knee 331 may be used to accurately design the prosthetic leg.

The artificial foot 335 used with the prosthetic leg will also be a stock item. Like the artificial knees, digital representations of the various different types of feet may be available. The proper foot may also be selected for the patient by the prosthetist and the digital representation can be used in the design of the prosthetic leg. For example, the foot 335 shown in FIG. 3 is made of a flexible material to provide energy storage and cushioning when compression forces are applied to the heel 341 and toe 343. This type of foot may be particularly useful for a highly active person who would like to run regularly. Alternatively, the fairing that is placed over the foot 335 can be based upon a mirror representation of the user's intact foot that is created by laser scanning the intact foot as described above.

The placement of the artificial knee 331 and foot 335 relative to the end of the amputated limb 209 are specified by the prosthetist and input into the CAD program. These components can be displayed within the prosthetic leg on a computer. The CAD program can manipulate the components to enlarge, rotate, add or remove or change components and show the movement of the prosthetic leg. All internal mechanical design information can be saved in computer readable format for future modification or prosthetic fabrication.

Figure 4:
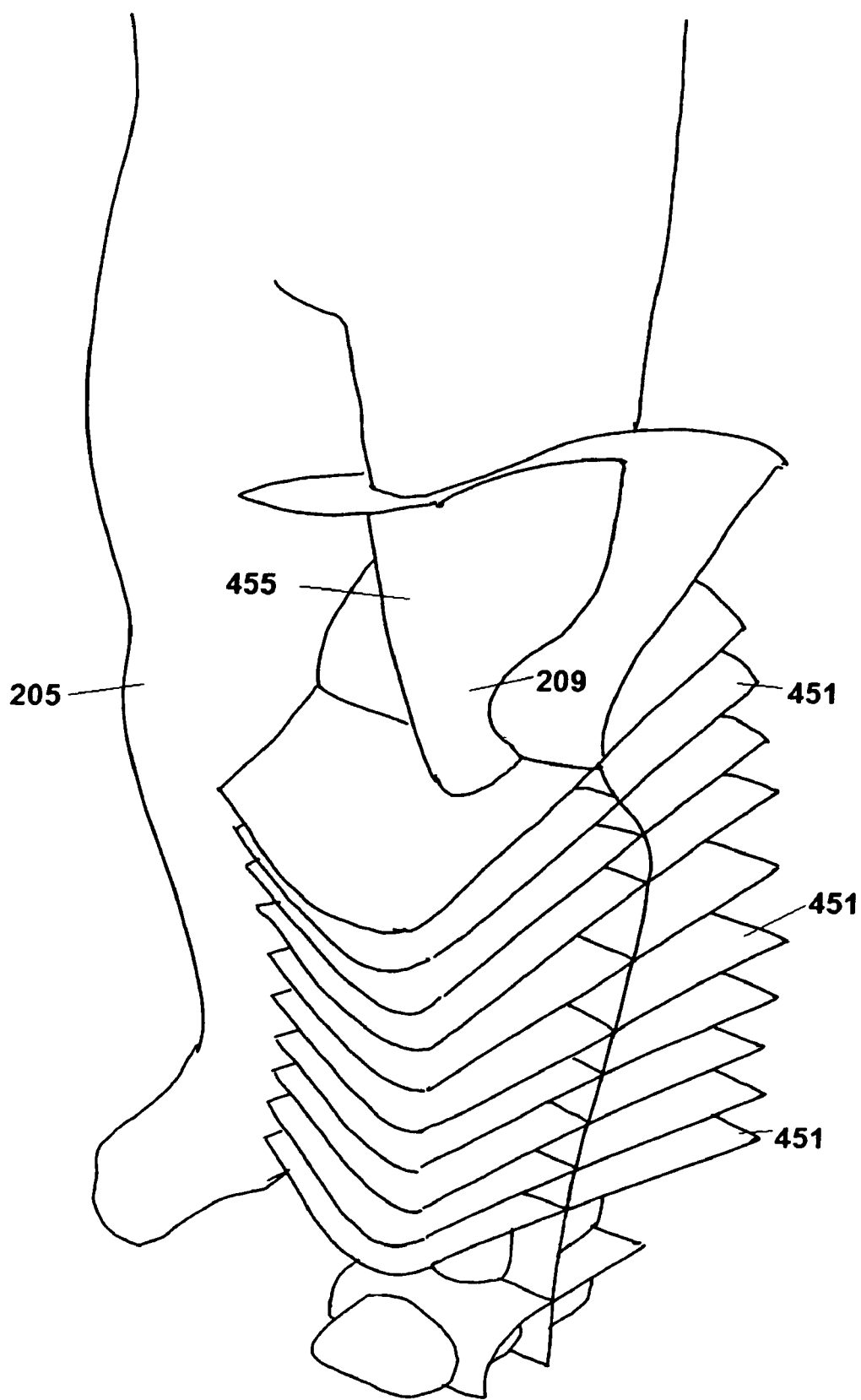
FIG. 4 is a view of load bearing components surrounded by templates used to design the prosthetic leg.

The internal mechanical component data and mirror image surface data can be joined together in a virtual prosthetic leg created by the prosthetist with the CAD program. The joining of the surface data and the internal mechanical components can be done in different ways. In an embodiment, the outer surface is a non load bearing structure fairing that is made of a thin material and references the geometry taken from the mirror image shape of the sound side leg. The fairing can be coupled to a series of cross section templates and longitudinal members that form an internal framework that are attached to the internal mechanical components. Alternatively, the framework can be exposed to simply be an exposed lattice that holds the form of the leg. In this embodiment, the pants will lay over the framework surface as though it were the real leg contour. The human eye reads the outer form of a lattice framework almost as though it is solid. The outer surface may not be load bearing, so the internal components and outer fairing can be distinct structures. With reference to FIG. 4, the non load bearing outer surface embodiment of the prosthetic leg is illustrated. Templates 451 are placed around the internal components in a configuration that the designer thinks would make an appealing form. The templates may not be mechanical or load bearing, so they can be arranged in any manner along the length of the leg. In this example, each template 451 extends beyond the exterior surface and each is trimmed to the corresponding surface of the mirror scan data 455 for the sound side limb. The mirror scan data 454 is placed around the prosthetic leg and intersects each of the templates 451. Because the mirror scan data 453 and templates 451 are illustrated in a virtual space, they can pass through each other during the design phase.

Figure 5:
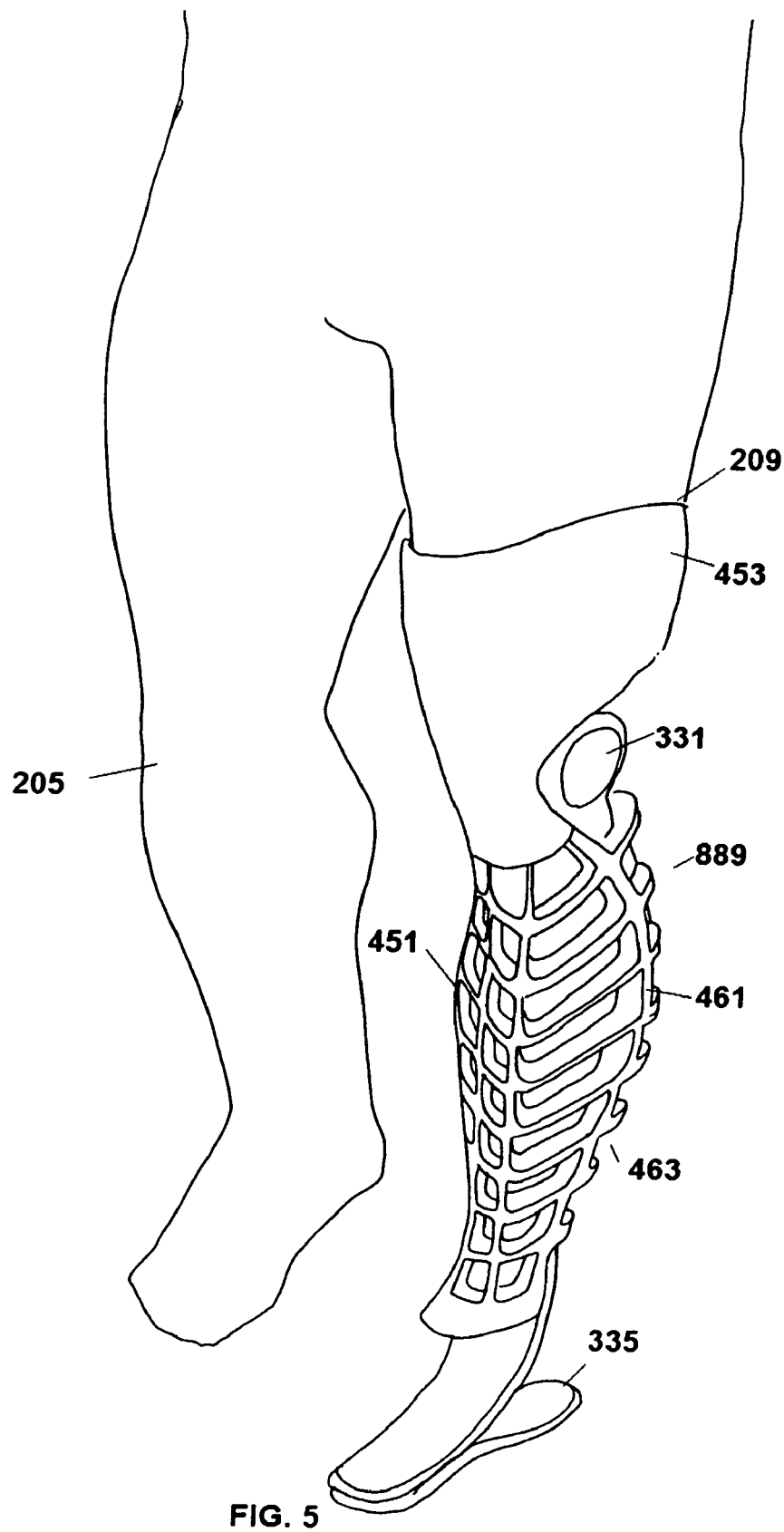
FIG. 5 is a view of the framework surrounding the load bearing components trimmed to the desired shape by the surface mirrored from scan data taken from the sound side leg.

With reference to FIG. 5, the outer surface fairing embodiment of the prosthetic leg 889 is shown with the fairing 453 removed below the knee 331. The templates 451 are cut to remove the portions of the templates 451 that extend beyond the mirrored scan data 455. The templates 451 and longitudinal members 461 provide an internal framework 463 that helps to maintain the shape of the fairing 453. The internal framework 463 may provide internal structure, or may simply give a certain style to the product.

Figure 6:
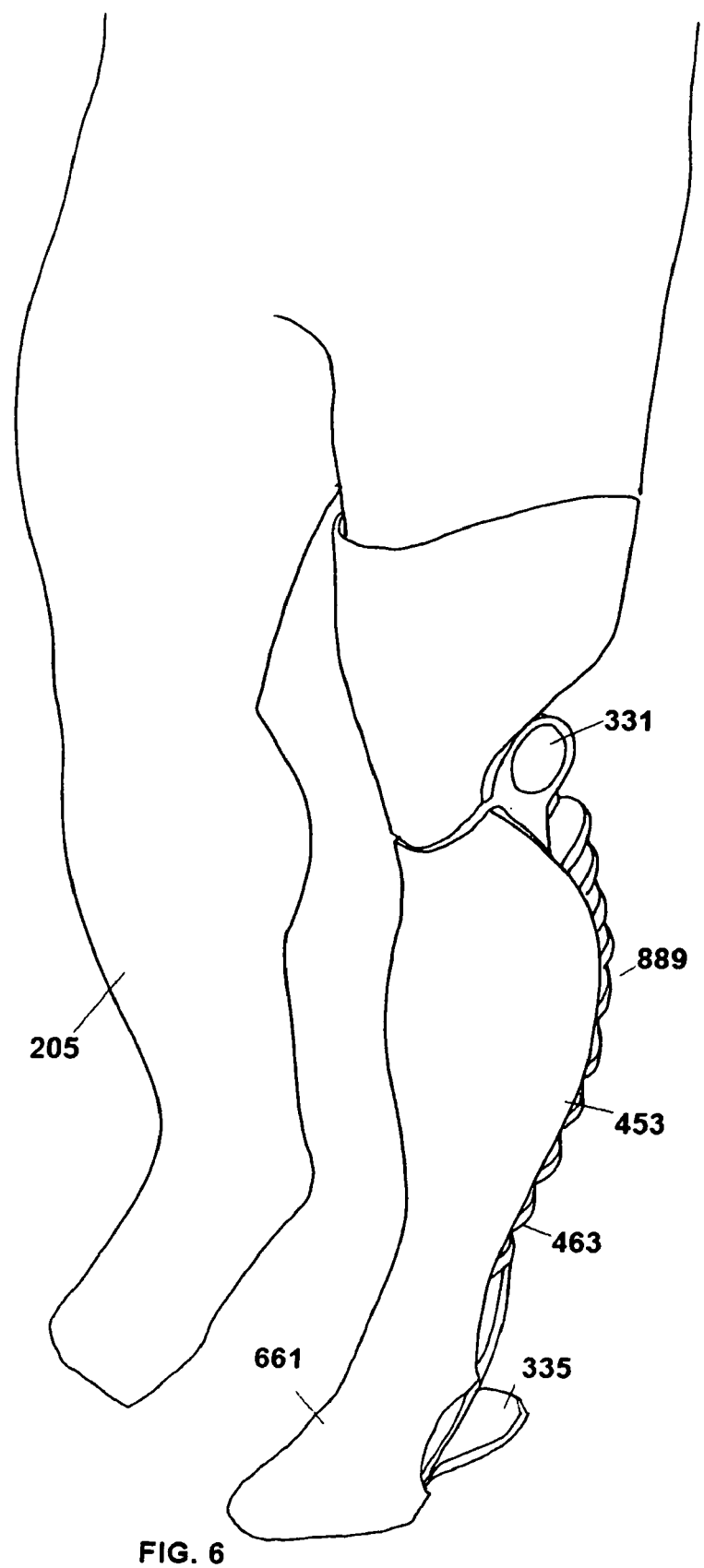
FIG. 6 is a view of a fairing placed over the framework of the prosthetic leg.

The designer can also design the fairing 453 to be flexible in areas of the prosthetic leg that move. With reference to FIG. 6, the shin fairing 453 is placed over the frame 463 and foot 335 of the prosthetic leg 889. The non load bearing fairing 453 may be made of a high strength flexible polyamide such as Nylon 6 or 12. In this embodiment, the fairing 453 wraps around a part of the shin and calf of the prosthetic leg. The fairing 453 also bends with any expected movement of the foot 335. Alternatively, the knee can have a break so the does not have to bend 130 degrees. As illustrated, the fairing 453 can be designed to have a narrow section that only covers the front of the knee 331. The fairing 453 may also be designed to only cover the front of the foot 335 but not the sides which allows for easier movement.

Figure 7:
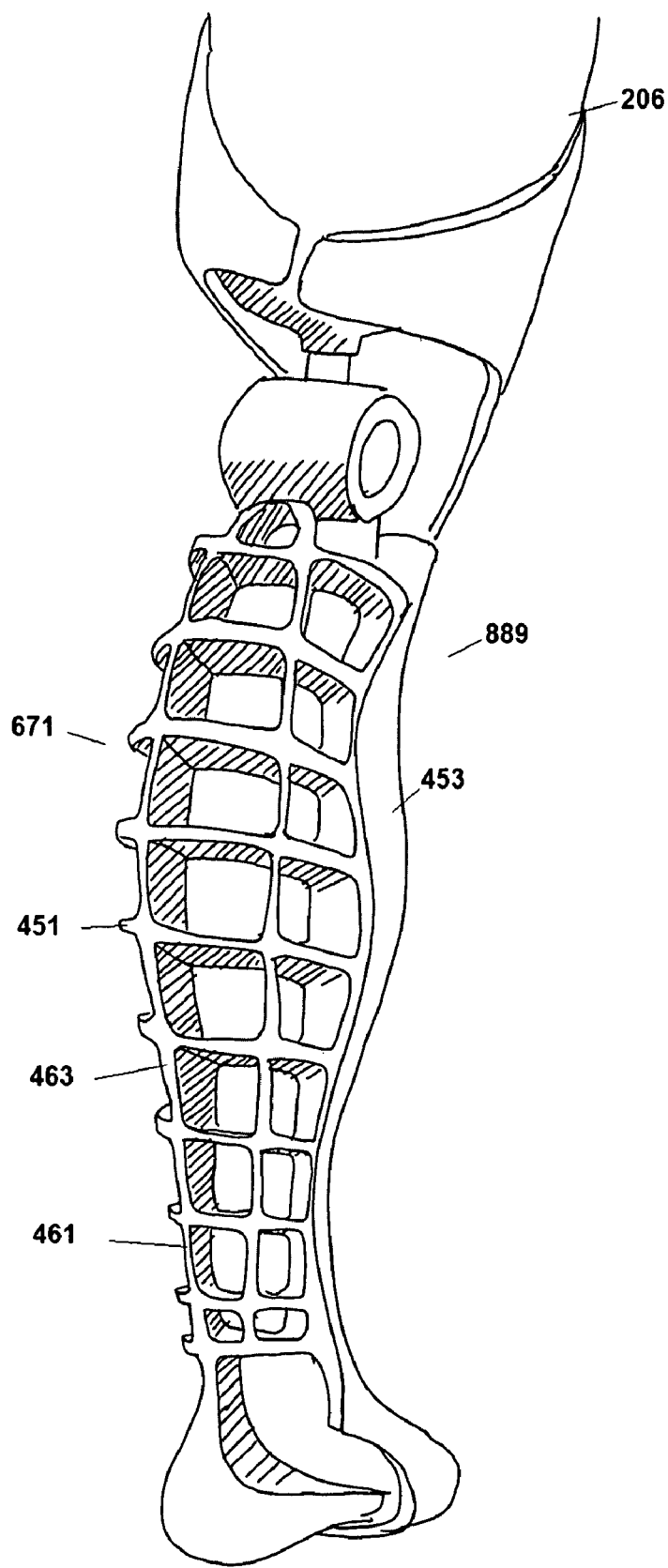
FIG. 7 is a rear view of a shin fairing showing both the load bearing sub structure and the fairing which surrounds a part of it.

With reference to FIG. 7, the rear portion of the prosthetic leg 889 is illustrated. The fairing 453 wraps almost fully around the upper portion of the prosthetic leg 889 covering the end of the amputated limb 206 and socket. The fairing 453 does not have to cover the calf portion 671 and the template 451 and longitudinal members 461 that form the framework 463 can be exposed, for aesthetic reasons. Like the templates 451, the longitudinal members 461 may extend from the inner load bearing member to the intersection with the mirror scan data. In other embodiments, the prosthetic designer can extend the fairing 453 around the calf portion 671 or add a separate fairing that wraps around the calf portion 671 of the prosthetic leg 889.

Figure 8:
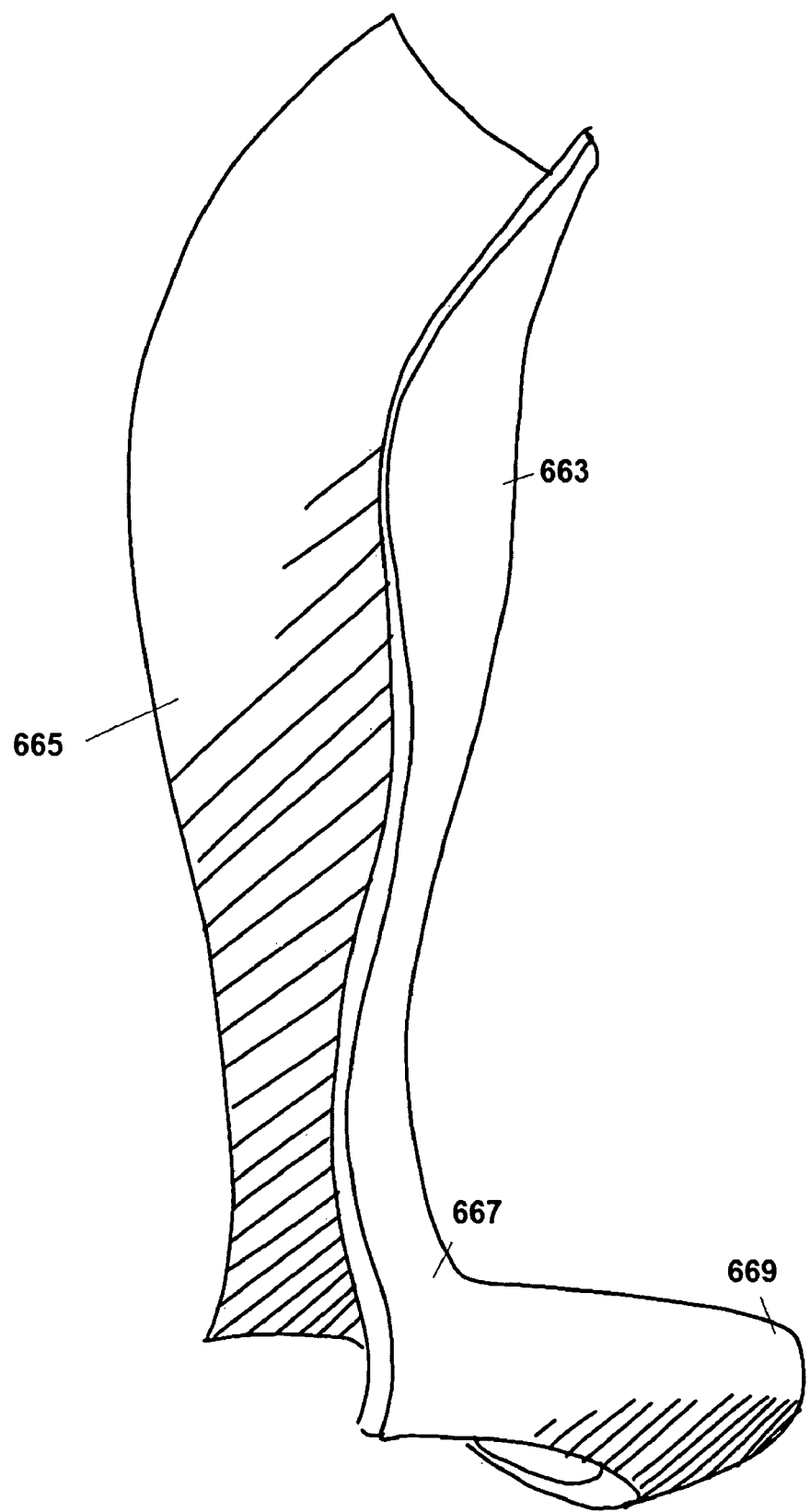
FIG. 8 is a rear view of the shin fairing.

With reference to FIG. 8, an inner view of a fairing 663 is illustrated that only covers the shin of the prosthetic leg and does not extend above the knee. The fairing 663 was designed to flex at the ankle and attach to the foot portion of the prosthetic leg. The thickness of the fairing 663 can be adjusted by the prosthetic designer. Because a thinner material is more flexible, the areas that are designed to flex may be designed with a thinner wall than the sections of the fairing 663 that do not move.

Figure 9:
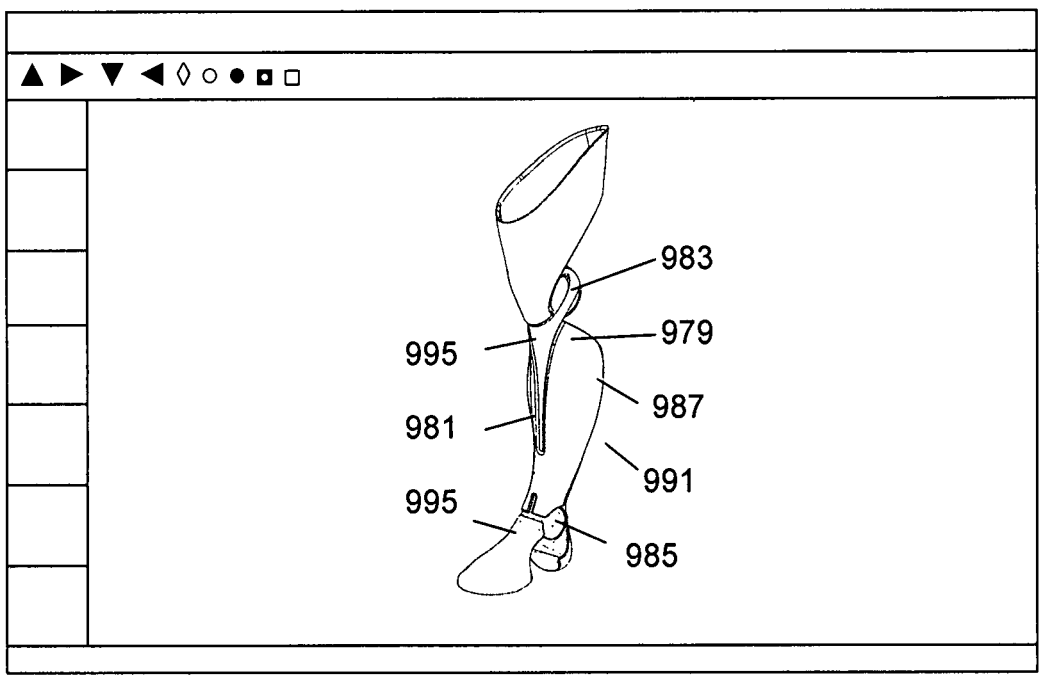
FIG. 9 illustrates a computer screen displaying a prosthetic leg design.

In the previously disclosed embodiments, CAD software has been used to create the framework and fairing that are mounted around an internal load bearing member or a framework that has a more dense 'core' portion that is load bearing. The outer framework provides a symmetric shape that gives form to the leg overall. The fairing mounts to the outer framework. In other embodiments, the outer surface of the leg is bonded to the internal framework. A removable fairing part can be mounted to the outer surface. With reference to FIG. 9, a prosthetic leg 987 having an external fairing 881 that is removably attached to an internal framework is illustrated, is the fairing 881 and prosthetic leg 987 were designed using a CAD program. The prosthetic leg 987 is attached directly to the knee joint 983 and the foot joint 985. In this embodiment, the fairing was designed as a separate component that is placed over the framework of the prosthetic leg 989.

In some cases, the user may wish to alter the design of the leg and fairing so that the prosthetic leg is a sculptural form that references the mirrored form of the sound side leg, but does not literally recreate the geometry of the sound side leg. The user may also want to have multiple interchangeable fairings for the prosthetic leg. The industrial designer creates a leg template, and decides which variables depend on the geometry of the user—knee location, shoe size, etc—and which can be open to user customization—fairing panel, surface finish, tattoo or graphic detail, etc. The designer decides on those parameters, and the user decides from within their options.

In an embodiment, the CAD system can include a graphical user interface (GUI) that allows the prosthetic designer to easily change the appearance of the leg and fairing. The GUI may be a special, custom, proprietary application, or it may simply be a CAD model that is built inside Pro/E. The GUI can have controls that allow the fairing and leg to be viewed with specific colors, materials, markings and surface features. Within each selected color, the prosthetic designer can also change the appearance by adding color effects such as: opaque, translucent, iridescent and metallic. The GUI can also have controls that allow the leg to be viewed with metal plated sections such as chrome, zinc, gold, silver, nickel and other alloys. A GUI control can also be used to give the surface of the prosthetic leg surface finish. The system can allow the prosthetic designer to see the prosthetic leg with a flat, matte, gloss, semi gloss, reflective, brushed, polished, textured or other finish. These modifications can be made to the entire fairing and leg or any exposed portions. The user can select the desired surface appearances. In an embodiment, the prosthetist may assist the user with the design process. In other embodiments, the design of the fairing can be done online, in a manner that is similar to the way a BMW Mini can be customized in real time, online. The CAD program will quickly display the virtual prosthetic leg and fairing with all the desired features. The designer and user can check all of the details of the prosthetic design prior to fabrication.

With reference to FIG. 9, an example of a personalized prosthetic leg 987 and fairing 991 design is illustrated. In this example, the industrial designer has developed a prosthetic leg 987 is partially covered with a matte nickel finish 995 that is applied to the outer surface of the leg 987. In this embodiment, the nickel finish 995 is applied to the knee joint 983 and the foot joint 985. In addition to being ornamental, the smooth nickel finish 995 on the knee joint 983 and the foot joint 985 can also provide a smooth sliding surface that improves the movement of the leg 987. The nickel finish 995 is also applied to the center section of the shin and around the top of the leg 987 as an ornamental feature. The industrial designer has also used the CAD program to design a black leather fairing 991 that smoothly wraps around most of the leg 987.

Figure 10:
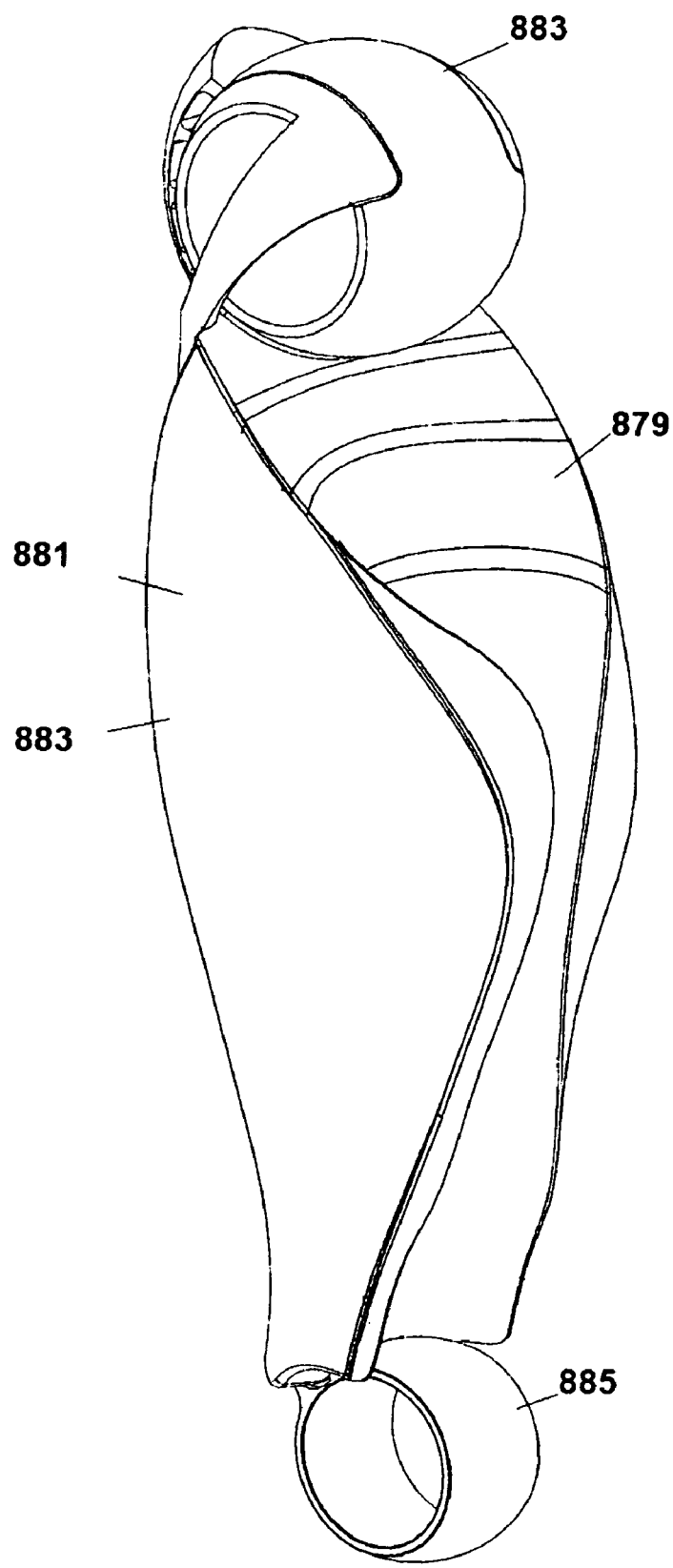
FIG. 10 is a view of (one embodiment of) a prosthetic leg.

In addition to changing the color and finish of the fairing and surface, the industrial designer can also modify the outer surface of the prosthetic limb. With reference to FIG. 10, an example of a surface modification is illustrated. In this example, the prosthetic designer has added a recessed surface 879 in the prosthetic leg 881 that extends along a portion of the calf. The recessed surface 879 is illustrated as a smooth concave. In other embodiments, the surface of the prosthetic leg can be modified by the prosthetic designer to extend above the mirror image surface. When the prosthetic designer completes the designs of the prosthetic leg and fairing, the design data produced by the CAD software can, when coupled with the unique data of the mirrored scan data taken from the sound side leg, be used to create a unique and custom fabricated the leg and fairing. Rapid prototyping is a general category of systems that uses digital design data and software to fabricate the components from various types of materials including metals, plastics and sand. These machines most often use an energy beam that is deflected across a bed of liquid or powdered material. The exposure to the energy beam causes the material to fuse together and harden. These fabrication machines are able to create all custom prosthetic limb components.

In order to fabricate the prosthetic leg components with the rapid prototyping machines, the CAD design data must be modified. The normal CAD design data for a component is converted into many parallel cross sections of vector data that extend along the length of the component. The data transmitted between the CAD software and the fabrication machine approximates the shape of a component cross sections through many connected triangular facets. Smaller facets produce a higher quality surface but require more time to calculate and can create very larger manufacturing data sets. The output of the CAD design program can be a standard STL file that is an export option, similar to a JPG export or any other file format.

The vector data for the component cross sections is read by a rapid prototyping scanner controller that converts the vector data to movement information which is sent to the energy beam scanhead. In a laser beam embodiment, the rapid prototyping machine includes a scanhead having two mirrors that deflect the laser beam in the X and Y coordinates over a bath of material. The fabrication information is then used to control the print head cross section to create each component cross section successively. The scanhead controller reads the fabrication data and causes the print head to expose successive layers of liquid, powder, or sheet material to precise patterns of laser light. Once the layer is completely formed, the component is moved into the bath so a thin layer of the material covers the previously formed layer. The process is repeated many times with new layers formed and fused to the previously formed layers. In an electron beam embodiment, an eletron beam is deflected over a bath of material in the X and Y coordinates with magnetic fields. The component cross sections are sequentially formed until the component fabrication is completed.

Figure 11:
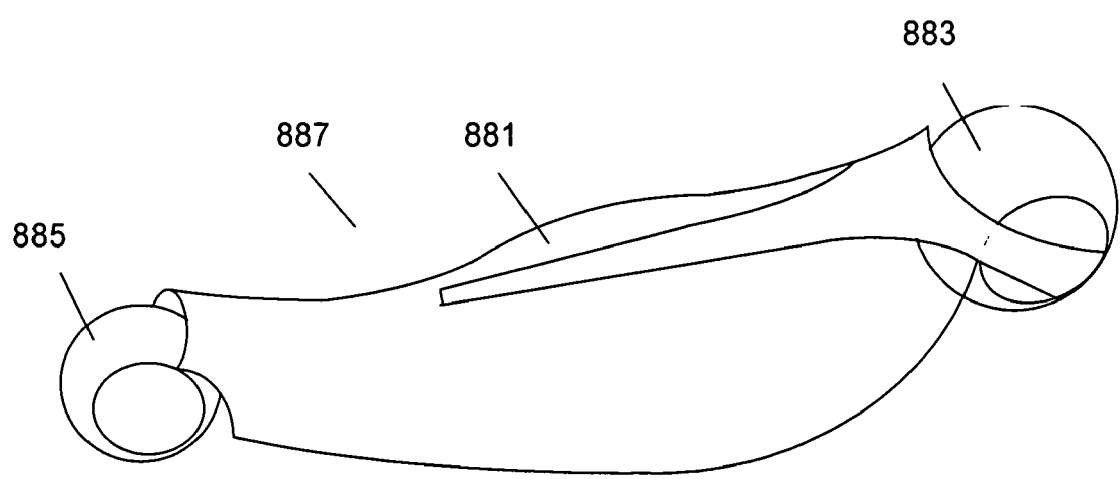
FIG. 11 is a view of a prosthetic leg having a load bearing exterior surface.

The primary advantage to additive fabrication rapid prototyping is the ability to create very complex shapes and geometric features such as the internal framework of the templates and longitudinal members within the prosthetic leg. A light weight and strong prosthetic limb can be made with a rapid prototyping machine from plastic materials such as photopolymers. FIG. 11 illustrates a completed photopolymer leg 887 that was fabricated using a rapid prototyping machine.

The rapid prototyping process can be applied to various materials including thermoplastics, photopolymers, metal powders, eutectic metals, titanium alloys and other materials. Examples of some suitable rapid prototyping machines include: laser sintering machines by EOS GmbH, electron beam sintering machines by Arcam AB and laser stereo lithography machines by 3D Systems Corp. Similar fabrication processes are known by the names: additive manufacturing, rapid manufacturing, layered manufacturing, 3D printing, laser sintering, electron beam melting (EBM), etc. All of these fabrication process use a similar operating principle of scanning an energized beam over a bath of material to solidify a precise pattern of the material to form each layer until the entire component is complete.

Another possible fabrication process is fused material deposition (FDM). FDM works on an "additive" principle by laying down material in layers. A plastic filament or metal wire is unwound from a coil and supplies material to an extrusion nozzle which can turn on and off the flow. The nozzle is heated to melt the material and can be moved in both horizontal and vertical directions by a numerically controlled mechanism, directly controlled by a CAD software. In a similar manner to stereolithography, the model is built up from layers as the plastic hardens immediately after extrusion from the nozzle.

While rapid prototyping is the preferred fabrication method there are other possible methods for forming the prosthetic limb components. In an embodiment, the design information can be used by a computer numerical control (CNC) which controls a machine tool to fabricate components from a solid block of material by the selective removal of material. A computer controller reads programming instructions and drives a powered mechanical cutting tool. The CNC system numerically directs interpolation of the surface data and controls a cutting tool to create the component. The CNC process is a sculpting process that is much less efficient than the rapid prototyping fabrication process and can produce a substantial amount of scrap material.

The fairing can also be fabricated using the design data. The most appropriate fabrication process may depend upon the fairing cladding material. The fairing will typically be a hard plastic shell such as polyamide. The cladding can be leather, fabric, suede, or any material that suits the user's tastes. For example, if the fairing is made from a flexible material, the fairing design data can be used to cut the fairing from flat sheet stock. The fairing design data can be used by a computer controlled machine to precisely cut a sheet of material into the shape of the fairing. The fairing material such as leather, fabric and other sheet material can be cut by a CNC, laser, etc. The cut material can then be applied to the fairing panel, like the leather over a bicycle seat. The fairing panel can then fastened by the user to the prosthetic leg. Like the leg component fabrication method described above, the rapid prototyping machine would use the fairing design data to fabricate the fairing from a sequential series of cross section layers.

Another typical requirement of the prosthetic limb is color. The desired color can also be applied to the prosthetic component or fairing during the fabrication process. In an embodiment, the color of the fairing and leg components can be applied through pigments that are mixed with materials used to fabricate the leg. The colors that will exist throughout the structures cannot be removed. Alternatively, the color may be applied to a leg component in a separate painting, dying, deposition or other coloring process to form a color layer over the outer surfaces of the leg and fairing.

In another embodiment, a metal or ceramic layer can be deposited onto the outer surfaces of the leg and fairing. The method used to deposit the metal layer can depend upon the base material of the leg or fairing. The metal layer can be deposited on a non-conductive plastic component through an electroless or chemical plating process. If the component being plated is a conductive material, an electro-chemical plating process can be used to deposit the metal layer. After the color or metal layers are applied to the prosthetic components, additional surface finishing processes can be performed. Examples of surface finishes include flat, matte, gloss, semi gloss, reflective, brushed, polished and textured that can be applied through known mechanical or chemical processes. A protective clear plastic or paint coating may also be applied to the leg and fairing.

The last fabrication step can be attaching the fairings to the prosthetic leg. The fairing can be attached in many different ways. As discussed, in the preferred embodiment, the fairing is a removable structure that can be easily replaced by the user. Releasable fasteners can be used to hold the fairing to the member. Examples of releasable fasteners include bolts, buckles, buttons, clamps, clips, pins, retainers, rivets, bands, snaps, stitching, straps, tacks, ties, zippers, etc. The fairing can also be attached to the leg with an adhesive. In an alternative embodiment, the fairing is permanently attached to the leg.

Figure 12:
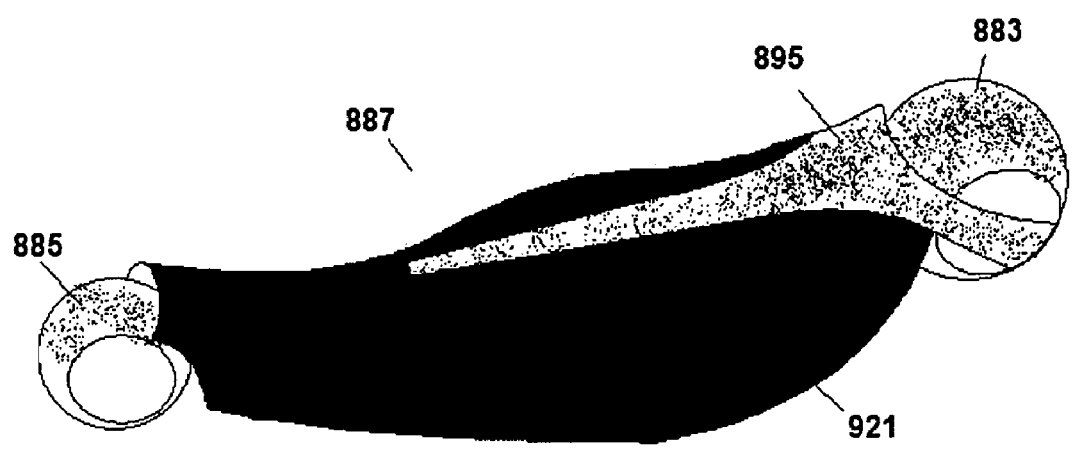
FIG. 12 is a view of a prosthetic leg having a nickel finish and an attached leather fairing.

FIG. 12 illustrates a prosthetic leg 887 after the surfaces have been metal plated and the fairing has been attached. The exposed areas of the prosthetic leg 887, the knee joint and ankle joint, have a nickel finish 895. The nickel finish was applied over the plastic leg using an electroless nickel plating process. In this embodiment, the fairing 921 is a semi-rigid plastic part that is wrapped in other materials, like a bike seat. The material applied to the fairing was cut from a smooth black leather material. The fairing 921 is attached to the outer surface of the leg 887 within a recessed area that extends around the shin and calf sections. The fairing 921 attachment mechanism allows the fairing 921 to be removed and replaced with another fairing.

It will be understood that the inventive system has been described with reference to particular embodiments, however additions, deletions and changes could be made to these embodiments without departing from the scope of the inventive system. For example, the same processes described for designing and fabricating a prosthetic leg can also be applied to the design and construction of a prosthetic arm that can include a socket, an elbow, an elongated member and an artificial hand. Although the prosthetic limbs that have been described include various components, it is well understood that these components and the described configuration can be modified and rearranged in various other configurations.

What is claimed is:

1. A method for creating a prosthetic limb comprising:
obtaining surface data for an intact limb;
creating a prosthetic limb design having an outer surface that corresponds to a mirror image of the surface data;
producing limb fabrication data and fairing fabrication data from the prosthetic limb design;
using the limb fabrication data, fusing a plurality of material particles together to form the prosthetic limb; and using the fairing fabrication data to fabricate a fairing, an inner surface of the fairing fitting around the outer surface of the prosthetic limb that corresponds to the mirror image of the surface data.

2. The method of claim 1 further comprising:
applying a metal layer to an outer surface of the fairing.

3. The method of claim 1 further comprising:
applying a colored layer to an outer surface of the fairing.

4. The method of claim 1 further comprising:
applying a colored dye to an outer surface of the fairing.

5. The method of claim 1 further comprising:
applying a metal layer to an outer surface of the prosthetic limb.

6. The method of claim 1 further comprising:
applying a colored layer to an outer surface of the prosthetic limb.

7. The method of claim 1 wherein the prosthetic limb design includes a framework having a plurality of openings.

8. The method of claim 1 wherein the fairing is discontinuous, the fairing covering a first portion of the prosthetic limb and not covering a second portion of the prosthetic limb.

9. The method of claim 1 further comprising:
covering a first portion of the prosthetic limb with the fairing; and
leaving a second portion of the prosthetic limb exposed.

10. The method of claim 9 wherein the first portion of the prosthetic limb is a front surface of the prosthetic limb and the second portion of the prosthetic limb is a back surface of the prosthetic limb.

11. The method of claim 9 wherein the first portion of the prosthetic limb is a front surface of the prosthetic limb and the second portion of the prosthetic limb is a side surface of the prosthetic limb.

12. The method of claim 1 wherein the prosthetic limb includes a framework having cross section templates.

13. The method of claim 1 wherein the fairing includes a metal material.

14. The method of claim 1 further comprising:
performing one or more of the finishing processes on the fairing: plating, texturing, brushing, polishing or sand blasting.

15. The method of claim 1 further comprising:
applying a graphical design to the fairing.

16. The method of claim 1 wherein the fairing includes a recessed surface.

17. A method for creating a prosthetic limb comprising:
obtaining surface data for an intact limb;
creating a prosthetic limb design having an outer surface that corresponds to a mirror image of the surface data;
producing limb fabrication data and fairing fabrication data from the prosthetic limb design;
using the limb fabrication data, fusing a plurality of material particles together to form a plurality of layers that are fused to form the prosthetic limb; and
using the fairing fabrication data to fabricate multiple interchangeable fairings, an inner surface of the fairings fitting around the outer surface of the prosthetic limb that corresponds to a mirror image of the surface data.

18. The method of claim 17 wherein the prosthetic limb design includes a framework having a plurality of openings.

19. The method of claim 17 wherein the interchangeable fairings are discontinuous, the interchangeable fairings covering a first portion of the prosthetic limb and not covering a second portion of the prosthetic limb.

20. The method of claim 17 further comprising:
covering a first portion of the prosthetic limb with the interchangeable fairings; and
leaving a second portion of the prosthetic limb exposed.

21. The method of claim 20 wherein the first portion of the prosthetic limb is a front surface of the prosthetic limb and the second portion of the prosthetic limb is a back surface of the prosthetic limb.

22. The method of claim 20 wherein the first portion of the prosthetic limb is a front surface of the prosthetic limb and the second portion of the prosthetic limb is a side surface of the prosthetic limb.

23. The method of claim 17 wherein the prosthetic limb includes a framework having cross section templates.

24. The method of claim 17 wherein the fairings include recessed surfaces.

* * * * *